United States Patent [19]

Hallot et al.

[11] Patent Number: 4,499,092
[45] Date of Patent: Feb. 12, 1985

[54] DERIVATIVES OF 4-PHENYL QUINAZOLINE ACTIVE ON THE CENTRAL NERVOUS SYSTEM

[75] Inventors: André Hallot, St. Gely du Fesc; Kathleen Bizière, Clapiers, both of France

[73] Assignee: Sanofi, France

[21] Appl. No.: 435,230

[22] Filed: Oct. 19, 1982

[30] Foreign Application Priority Data

Oct. 21, 1981 [FR] France ............... 81 19767

[51] Int. Cl.³ .............. A61K 31/505; C07D 239/84
[52] U.S. Cl. .................. 514/254; 544/283; 544/292
[58] Field of Search .............. 544/292; 424/250, 251

[56] References Cited

U.S. PATENT DOCUMENTS

| 3,305,553 | 2/1967 | Hoefle et al. | 544/292 |
| 3,509,141 | 4/1970 | Walker | 544/292 |
| 4,183,932 | 1/1980 | Yamamoto et al. | 544/292 |

FOREIGN PATENT DOCUMENTS

| 894239 | 2/1972 | Canada | 544/292 |
| 40-20866 | 9/1965 | Japan | 544/292 |

OTHER PUBLICATIONS

Walker, "Chemical Abstracts", vol. 73, 1970, Col. 3927a.
Shenoy, "Chemical Abstracts", vol. 84, 1976, Col. 84:90191z.
Yamamoto, et al., "Chemial Abstracts", vol. 89, 1978, Col. 89:43488u.
Yamamoto, et al., "Chemical Abstracts", vol. 89, 1978, Col. 197593n.

Primary Examiner—Glennon H. Hollrah
Assistant Examiner—James H. Turnipseed
Attorney, Agent, or Firm—Ostrolenk, Faber, Gerb & Soffen

[57] ABSTRACT

The present invention relates to novel derivatives of 4-phenyl quinazoline of general formula:

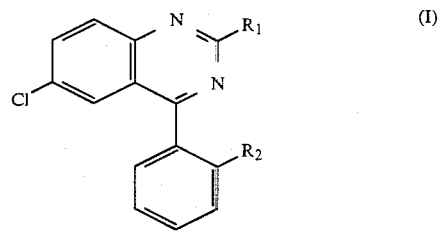

in which $R_2$ is H or halogen or $R_1$ is a hydroxyamino derivative of type

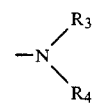

in which at least $R_3$ or $R_4$ comprises an OH group or

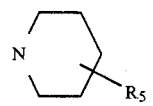

in which $R_5$ comprises an OH group or

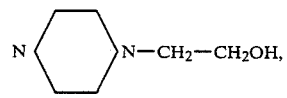

it also relates to the drugs which may be used as minor tranquilizers, hypnotics and antiepileptics containing a product of formula (I).

21 Claims, No Drawings

DERIVATIVES OF 4-PHENYL QUINAZOLINE ACTIVE ON THE CENTRAL NERVOUS SYSTEM

The present invention relates as novel industrial products to derivatives of 6-chloro 4-phenyl quinazoline substituted in 2 position by a hydroxyamino group, as well as to the process for preparing same and to the application thereof as drugs.

The new compounds according to the invention respond to the general formula:

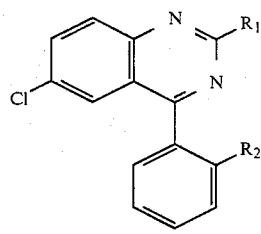

in which
R₁ is selected from
(a) a group

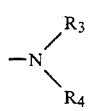

in which
R₃ represents hydrogen or a group —(CH₂)ₙOH and R₄ represents a group (CH₂)ₙOH where n designates an integer equal to 2, 3 or 4;
(b) a group

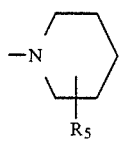

where
R₅ designates a group —(CH₂)ₘ—OH (m being an integer which may vary from 0 to 2) situated in meta or para position;
(c) a group

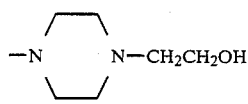

where
R₂ represents an atom of halogen, preferably chlorine or fluorine, or R₂ may be hydrogen in the case of R₁ being

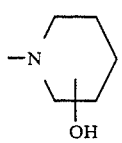

Compounds (I) furnish soluble salts with the mineral or organic acids. These salts, with pharmaceutically acceptable acids, form an integral part of the invention.

Compounds (I) may be prepared from 6-chloro 4-phenyl 2-quinazolone suitably substituted (I) according to the reaction scheme:

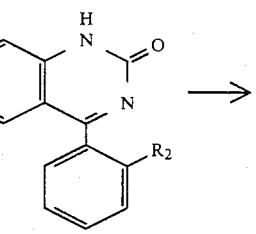

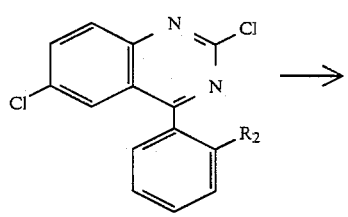

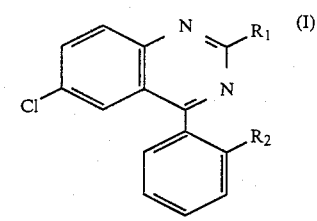

By action on the quinazolone 1 of a chlorinated derivative of phosphorus, the chlorinated derivative 2 is obtained in position 2. Phosphorus oxychloride is most often used. Operation may be carried out within an inert solvent such as an aromatic hydrocarbon (benzene or toluene) but it is most often preferred to use an excess of oxychloride as solvent. Reaction takes place at a temperature of between 60° and 120° C. and, most often, at the boiling temperature of the solvent used.

From the chlorinated derivative 2, by action of an amine R₁H in considerable excess within an inert solvent such as ethanol, the corresponding compound (I) is obtained. Operation generally consists in heating to the boiling temperature of the solvent.

The salts of compounds (I) are usually obtained by salifying the base, hot, by a stoichiometric quantity of acid within a suitably selected solvent so that the salt formed crystallizes by cooling.

The starting quinazolones 1 are known compounds which may in particular be prepared by action of potassium cyanate on a suitably substituted 2-amino 5-chloro benzophenone.

The following non-limiting examples are given by way of illustration for the preparation of compounds (I) according to the method indicated hereinabove.

EXAMPLE 1

6-chloro 4-(2-chloro phenyl) 2-(4-hydroxy 1-piperidinyl)quinazoline, hydrochloride (CM 40331)

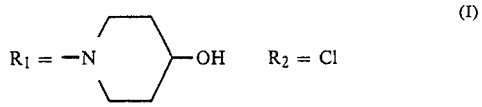

(a) 2,6 dichloro 4-(2-chloro phenyl)quinazoline

The mixture of 11.8 g of 6-chloro 4-(2-chloro phenyl) 2-quinazolone and 59 ml of phosphorus oxychloride is heated to reflux for 6 hours with stirring. The excess phosphorus oxychloride is evaporated in vacuo to dryness and the residue is poured onto a mixture of ice-water. The solid which separates is drained, washed with water then recrystallized from ethanol.

11.7 g of the expected product are obtained, m.p.: 175°–6° C.

(b) CM 40331

The mixture of 13.1 g of the product obtained hereinabove and 12.8 g of 4-hydroxy piperidine in 68 ml of ethanol is heated to reflux for 1 hour. The solvent is evaporated and the residue is taken up in water and then extracted with ethyl acetate. The organic solution is dried over sodium sulfate and the solvent is evaporated to dryness. The residue is dissolved in boiling isopropylic ether and allowed to crystallize by cooling.

10.5 g of base are thus obtained, m.p.: 129°–131° C.

Hydrochloride

The base obtained hereinabove (10.5 g) is dissolved in 70 ml of absolute ethanol and gaseous hydrochloric acid is added up to acid pH. The crystals formed are drained and recrystallized in absolute ethanol. Weight 10.6 g; m.p.: 212°–4° C.

EXAMPLES 2 to 11

(a) 2,6-dichloro 4-(2-$R_2$ phenyl)quinazoline

By operating as in Example 1(a), but by varying the starting quinazolone, the following are obtained in the same way:

2,6-dichloro 4-(2-fluoro phenyl)quinazoline; m.p.: 208°–210° C. (acetonitrile)

2,6-dichloro 4-phenyl quinazoline; m.p.: 159°–160° C. (ethyl acetate)

(b) From the various chlorinated derivatives mentioned previously and by varying the amine $R_1H$ used, the different compounds (I) shown in Table I are obtained, as indicated in example 1(b).

The products according to the invention were submitted to pharmacological tests with a view to determining the activity thereof on the central nervous system.

(1) Antiepileptic action

The antiepileptic action of the products according to the invention was in particular studied by the test of the antagonism of the convulsions induced by pentetrazol.

This test was carried out on naive female mice, OF1 (Iffa Credo, France) weighing 18 to 23 g.

The day before the experiment, the animals are marked, weighed, placed in 10's in macrolon cages (30×19×12 cm) and kept in the air-conditioned animal house until the day of the experiment. Food and drink are administered ad libitum. On the day of the experiment, the animals are placed in the laboratory where the experiment is to take place.

The products to be studied are suspended in 5% gum water and administered orally at the dose of 200 mg/kg (expressed in salt) to batches of 10 mice at a volume of 20 ml/kg. The controls receive the gum water alone.

One hour after administration of the products to be studied, the pentetrazol dissolved in distilled water is administered by the intraperitoneal route at the dose of 125 mg/kg at a volume of 20 ml/kg. Immediately after the injection of the convulsivant analeptic, the mice are placed in individual recipients (10×10×15 cm). One hour after administration of pentetrazol, mortality is recorded.

The results are expressed in percentage of animals having survived, i.e. in percentage of animals having been protected from the action of pentetrazol.

(2) Potentialization of the narcosis induced by pentobarbital

This test was carried out on naive female mice, OF1 (Iffa-Credo, France) weighing 18 to 23 g.

The day before the experiment, the animals are marked, weighed, placed in 10's in macrolon cages (30×19×12 cm) and kept in the air-conditioned animal house until the day of the experiment. Food and drink are administered ad libitum. On the day of the experiment, the animals are placed in the laboratory where the experiment is to take place.

The products to be studied are suspended in 5% gum water and administered orally at the dose of 120 mg/kg (expressed in salt) to batches of 10 mice at a volume of 20 ml/kg. The controls receive the gum water alone.

One hour after administration of the products to be studied, the pentobarbital (6% sodium pentobarbital) is administered at the dose of 20 mg/kg at a volume of 20 ml/kg. The number of animals having lost the righting reflex is noted. The results are expressed in % of animals which are asleep.

The results obtained on these two tests with the products of the invention are shown in Table II.

Furthermore, the products of the invention are only slightly toxic. All the products tested are totally atoxic at the dose of 500 mg/kg.

These products may be used in human therapeutics as minor tranquilizers, hypnotics and antiepileptic drugs.

The products may be presented in the Galenic forms corresponding to the oral route (powders, tablets, capsules . . . ) and to the parenteral route (injectable ampoules).

Dosage which varies depending on the disorders to be treated and on the mode of administration, will be progressive and will be between 100 and 600 mg per day in the adult.

The following Galenic preparation may be indicated by way of example:

| Capsule | |
|---|---|
| CM 40 331 | 0.050 g |
| Starch STA RX 1500 | 0.048 g |
| Magnesium stearate | 0.002 g |
| for 1 No. 3 capsule. | |

TABLE I

| Example N° | Code No. of the Product | R₁ | R₂ | Base or salt Melting point °C. (solvent of recrystallisation) |
|---|---|---|---|---|
| 2 | 40 332 | −N(CH₂CH₂OH)₂ | Cl | Hydrochloride 176-8 (isopropanol) |
| 3 | 40 411 | " | F | Base 144-6 (methanol) Hydrochloride 194-6 (isopropanol) |
| 4 | 40 416 | −N(piperidine)−OH (4-hydroxypiperidine) | F | Base 188-190 (methanol) |
| 5 | 40 451 | −NH−CH₂CH₂OH | Cl | Base 144-6 (ethyl acetate) |
| 6 | 40 621 | −NH−CH₂CH₂CH₂OH | Cl | Base 124-6 (ether) |
| 7 | 40 669 | −N(piperazine)N−CH₂CH₂OH | Cl | Base 118-120 (isopropylic ether) |
| 8 | 40 744 | −NH−(CH₂)₃CH₂OH | Cl | Base 126-8 (ethyl acetate) |
| 9 | 40 785 | −N(piperidine)−CH₂CH₂OH | Cl | Hydrochloride 192-5 (isopropanol) |
| 10 | 40 788 | −N(piperidine)-3-OH | Cl | Hydrochloride 210-2 (isopropanol) |
| 11 | 40 854 | −N(piperidine)−OH (4-hydroxypiperidine) | H | Hydrochloride 260-2 (ethanol at 96) |

TABLE II

| Code No. of the Product | Antagonism of Cardiazol (% of animals protected) | Narcosis % of animals which are asleep |
|---|---|---|
| 40 331 | 100 | 100 |
| 40 788 | 50 | 100 |
| 40 332 | 50 | 80 |
| 40 451 | 50 | 50 |
| 40 785 | 30 | 80 |
| 40 744 | 40 | 60 |
| 40 854 | 30 | 20 |
| 40 416 | 20 | 20 |
| 40 669 | 30 | 40 |
| 40 411 | 50 | 50 |
| 40 621 | 20 | 70 |

What is claimed is:

1. A compound of 4-phenyl quinazoline of the formula:

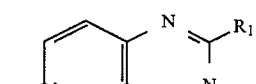

in which
R₁ is selected from
(a) a group

in which
R₃ represents hydrogen or a group —(CH₂)$_n$OH and R₄ represents a group (CH₂)$_n$OH where n designates an integer equal to 2, 3 or 4;
(b) a group

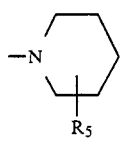

where
R₅ designates a group $-(CH_2)_m-OH$ (m being an integer which may vary from 0 to 2) situated in meta or para position;
(c) a group

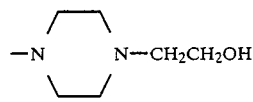

where
$R_2$ represents an atom of halogen, or $R_2$ may be hydrogen in the case of $R_1$ being

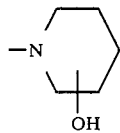

the salts with pharmaceutically acceptable mineral or organic acids thereof.

2. A compound according to claim 1 wherein $R_2$ is chlorine or fluorine.

3. A compound according to claim 1 wherein $R_1$ is said group (b), m is 0 and $R_2$ is hydrogen, chlorine or fluorine.

4. A compound according to claim 3 wherein $R_5$ is in the para position.

5. A compound according to claim 4 wherein $R_2$ is chlorine.

6. A compound according to claim 3 wherein $R_2$ is chlorine and $R_5$ is in the meta position.

7. A compound according to claim 1 wherein $R_2$ is chlorine and $R_1$ is $-NHCH_2CH_2OH$, $-NHCH_2CH_2CH_2OH$ or $-NH-(CH_2)_3CH_2OH$.

8. A compound according to claim 1 wherein $R_2$ is chlorine and $R_1$ is

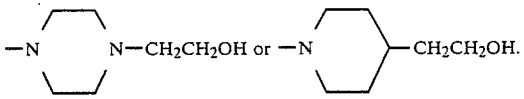

9. A compound according to claim 2 wherein $R_1$ is $-N(CH_2CH_2OH)_2$.

10. A compound according to claim 9 wherein $R_2$ is chlorine.

11. A pharmaceutical composition comprising a pharmaceutically acceptable carrier and a tranquilizing, hypnotic or anti-epileptic effective amount of at least one compound according to claim 1.

12. A pharmaceutical composition according to claim 11 wherein the amount of said compound is 100–600 mg.

13. A pharmaceutical composition according to claim 12 wherein $R_2$ is chlorine or fluorine.

14. A pharmaceutical composition according to claim 12 wherein $R_1$ is said group (b), m is 0 and $R_2$ is hydrogen, chlorine or fluorine.

15. A pharmaceutical composition according to claim 14 wherein $R_5$ is in the para position.

16. A pharmaceutical composition according to claim 15 wherein $R_2$ is chlorine.

17. A pharmaceutical composition according to claim 15 wherein $R_2$ is chlorine and $R_5$ is in the meta position.

18. A pharmaceutical composition according to claim 12 wherein $R_2$ is chlorine and $R_1$ is $-NHC_2CH_2OH$, $-NHCH_2CH_2CH_2OH$ or $-NH-(CH_2)_3CH_2OH$.

19. A pharmaceutical composition according to claim 12 wherein $R_2$ is chlorine and $R_1$ is

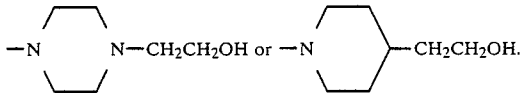

20. A pharmaceutical composition according to claim 13 wherein $R_1$ is $-N(CH_2CH_2OH)_2$.

21. A pharmaceutical composition according to claim 20 wherein $R_2$ is chlorine.

* * * * *